United States Patent
Ryu et al.

(10) Patent No.: US 8,637,097 B2
(45) Date of Patent: Jan. 28, 2014

(54) PHARMACEUTICAL COMPOSITION FOR TREATING NEPHROPATHY AND HEALTHY FOOD COMPRISING HERB EXTRACTS

(75) Inventors: Jei-Man Ryu, Seongnam-si (KR); Moon-Jung Leem, Anyang-si (KR); Yang-Kook Roh, Ansan-si (KR); Hwan-Bong Chang, Incheon (KR); Seong-Jun Oh, Seongnam-si (KR); Hyun-Yong Lee, Uiwang-si (KR); Sae-Kwang Ku, Suwon-si (KR); Hee-Bog Yang, Suwon-si (KR); Jung-Woo Rhee, Gunpo-si (KR); Yun-Jung Kim, Gwangmyeong-si (KR); Joo Byoung Yoon, Incheon (KR)

(73) Assignee: Dong Wha Pharm. Co., Ltd., Seoul (KR)

(*) Notice: Subject to any disclaimer, the term of this patent is extended or adjusted under 35 U.S.C. 154(b) by 0 days.

(21) Appl. No.: 13/334,583

(22) Filed: Dec. 22, 2011

(65) Prior Publication Data

US 2012/0093942 A1 Apr. 19, 2012

Related U.S. Application Data

(63) Continuation of application No. 11/814,716, filed as application No. PCT/KR2006/000337 on Jan. 31, 2006, now abandoned.

(30) Foreign Application Priority Data

Jan. 31, 2005 (KR) .................. 10-2005-0008649

(51) Int. Cl.
*A61K 36/00* (2006.01)
*A01N 65/00* (2009.01)

(52) U.S. Cl.
USPC ......................................... 424/773; 424/725

(58) Field of Classification Search
USPC .................................................. 424/725, 773
See application file for complete search history.

(56) References Cited

U.S. PATENT DOCUMENTS 5,916,555 A 6/1999 Lee et al.

FOREIGN PATENT DOCUMENTS

| JP | 07-017856 | 1/1995 |
|---|---|---|
| KR | 10-2002-23455 A | 3/2002 |
| KR | 10-2002-23456 A | 3/2002 |
| KR | 10-2002-63734 A | 8/2002 |
| KR | 2003-0088329 A | 11/2003 |
| WO | WO 98/19688 | 5/1998 |

OTHER PUBLICATIONS

Evans et al. "Diabetic Nephropathy" Clinical Diabetes vol. 18 No. 1 Winter 2000, 16 pages.*
Utsunomiya et al. "The Effect of Macrophage Colony-Stimulating Factor (M-CSF) on the Progression of Lipid-Induced in Diabetic Nephropathy" Journal of Diabetes and Its Complications 2995; 9:292-295.*
Lewis et al. "The Effect of Angiotensin-Converting-Enzyme Inhibition on Diabetic Nephropathy" The New England Journal of Medicine, vol. 329, No. 20, pp. 1456-1462, 1993.*
Andersen et al. "Optimal dose of losartan for renoprotection in diabetic nephropathy" Nephrol Dial Transplant, 17:1413-1418, 2002.*
Eastern Chinese Medicine Export Company, "Mulberry Bark," http://www.tcmtreatment.com/herbs/0-sangbaipi.htm, accessed on Sep. 7, 2010, 2 pages.
Flora of China, "Aralia Continentalis Kitagawa," http://www.efloras.org/florataxon.aspx?flora_id+2&taxon_id=200015155, acessed on Sep. 7, 2010, 1 page.
Kim et al., "Bombycis Corpus Extract Prevents Amyloid-beta-Induced Cytotoxicity and Protects Superoxide Dismutase Activity in Cultured Rat Astrocytes," Pharmacological Research, 2001, vol. 43, No. 1, 6 pages.
Kim et al., "Antihyperglycemic Constituent of Aralia elata Root Bark (II)—Isolation and Action of the Constituents," Kor. J. Pharmacogn., 1993, vol. 24, No. 3, pp. 219-222.
Ko et al., "Influence of Mori Radicis Cortex on the Renal Function of Dog," Takhak Hoeji, 1982, vol. 26, No. 4, pp. 197-208.
Li et al., "Natural Medicines Used in the Traditional Chinese Medical System for Therapy of Diabetes Mellitus," Journal of Ethnopharmacology, 2004, vol. 92, pp. 1-21.
Merriam-Webster.com, "Herb," accessed Sep. 7, 2010, 1 page.
Modern Chinese Med. and Clin. Appl., 1994, pp. 626-632.
Natural Medicines Comprehensive Database, "Kudzu," copyright 1995-2010, 3 pages.
Sigh et al., "The Effect of Quercetin, a Bioflavonoid on Ischemia-Reperfusion Induce Renal Injury in Rats," Arch. Med. Res., 2004, vol. 35, pp. 484-494.
Yoon et al., "The Effect of Bobbycis corpus on Streptozotocin-induced Diabetic Rats," J. Korean Soc. Hygienic Sci., 2000, vol. 6, No. 1-2, pp. 11-22.

* cited by examiner

*Primary Examiner* — Thane Underdahl
(74) *Attorney, Agent, or Firm* — Sughrue Mion, PLLC (57) ABSTRACT

Disclosed is a pharmaceutical composition and health food comprising herb extracts of one or more herbs selected from the group consisting of Puerariae Radix, Bombycis corpus and Araliae Continentalis Radix. The herb medicine of this invention comprising a single or mixed composition may be useful for the prevention and treatment of renal diseases as well as improvement of renal functions.

5 Claims, 1 Drawing Sheet

PHARMACEUTICAL COMPOSITION FOR TREATING NEPHROPATHY AND HEALTHY FOOD COMPRISING HERB EXTRACTS

This is a continuation application of U.S. Ser. No. 11/814,716 filed on Jul. 25, 2007, which is a national stage application under 35 U.S.C. §371 of PCT/KR06/000337 filed Jan. 31, 2006, which claims priority from Korean Patent Application No. 10-2005-0008649 filed Jan. 31, 2005; all of which are incorporated herein by reference.

TECHNICAL FIELD

This invention relates to a novel use of an herb extract for prevention and treatment of renal disease, wherein it comprises one or more herb medicines selected from the group consisting of Puerariae Radix, Bombycis corpus or Araliae Continentalis Radix. Therefore, the herb extract of this invention may be effectively used as a pharmaceutical composition or health food to prevent and treat renal disease.

BACKGROUND ART

Mammals have two kidneys, one on each side in the region of the mid to lower back. Each kidney is composed of about 1 million nephrons. A nephron is composed of a renal corpuscle and a renal tubule specialized for re-absorption and excretion.

Renal disease results from damage to the nephrons, causing them to not function properly. Renal failure can be divided into acute (a rapid onset) or chronic (slowly progressive over time).

Depending on the causes, a number of different diseases (e.g., glomerulonephritis or diabetic neuropathy associated with diabetic or hypertensive complications) can result in renal disease. It may be the direct result of an infection or a drug toxic to the kidneys.

Chronic renal failure is defined as either kidney damage or glomerular filtration rate of less than 50%. Irrespective of the initiating insult, this is invariably a progressive process that results in end-stage renal disease (ESRD). Over the years, ESRD may be a life-threatening disease caused by other complications in blood, nerve system, gastrointestinal system, and immune system as well as by infection or osteodystrophy.

The number of patients with renal disease is growing worldwide, but symptoms are often not apparent until renal failure is advanced. In Korea, there are about 450,000 people with renal failure and a total of patients including early-diagnosed ones are likely to further increase.

After ESRD occurs, renal replacement therapy is required, in the form of either dialysis or transplant. However, its wide use is restricted due to failure in treating the underlying cause of chronic renal failure in early and middle stage, and higher medical costs that are burdensome to patients and their family members.

Recently, many researchers at home and abroad have made intensive studies on the mechanism of impaired renal functions and as a result, some compounds with simple chemical structures have been made available as a means of controlling blood pressure and treating the original disease, whenever feasible. For instance, angiotensin converting enzyme (ACE) inhibitors are used, as they have been found to slow the progression to ESRD. Replacement of erythropoiesis stimulating factor (ESF) and activated vitamin $D_3$, two hormones processed by the kidney, is usually necessary. Nevertheless, the wide use of these drugs has been quite restricted due to higher drug costs and palliative therapy. In this context, there is urgent need for the development of novel drugs for treatment of renal disease in the pharmaceutical sector.

Recent drug development has focused on chemical platforms that have been derived from natural sources. With a combination of novel properties, structure and less toxicity, natural products today are most likely going to continue to exist and grow to become even more valuable as sources of new drug leads.

In keeping abreast of the current trends of drug development, the inventors have tested a number of herb medicines to ensure that they are effective for improving the renal function in patients with renal failure.

Puerariae Radix, which belongs to Leguminosae, a root in which the periderm of *Pueraria thunbergiana* is removed. This plant has been shown to possess lipid lowering (Modern Chinese Medicines and Clinical Application, 626-632, 1994) and anti-diabetic properties (Anti-senility Chinese Medicine and Pharmacology, 186-187, 1989).

Bombycis corpus, a batryticated silkworm and white-stiff silkworm, is a drug consisting of the dried larva of silkworm, *Bombyx mori*, dead and stiffened due to the infection of Beauveria. This natural product has been also shown to exhibit anti-diabetic action (Journal of the Korean Society for Hygienic Science, Vol. 6, No. 1, 2, 11-33 (2000)) with lipoprotein as an active ingredient.

Araliae Continentalis Radix, which belongs to Araliaceae, is a root of Araliae Continentalis. This natural product is pungent, bitter and soft in its nature and has a combination of properties such as tonics, anti-inflammatory and lipid lowering actions (Korean J. of Pharmacognosy, 24 (3), 219-222 (1993)). Araliae Continentalis Radix contains angelol B, nerolidol, ostehnol, osthol, Isoimperatorin, ferulin, and oleanolic acid.

The inventors have endeavored to screen a wide variety of promising herb medicines and health foods listed in the Korean Food Standard Code to find a potential for prevention and treatment of renal disease. As a consequence the inventors have discovered that Puerariae Radix, Bombycis corpus and Araliae Continentalis Radix may be useful for the improvement of renal functions and consummated this invention.

DISCLOSURE

Technical Problem

The object of this invention is to provide novel pharmaceutical and health food candidates to prevent and treat renal diseases, which are selected from herb medicines listed in the Korean Food Standard Code.

Technical Solution

This invention is to provide a pharmaceutical composition containing at least one and more herbs extracts which are selected from the group consisting of Puerariae Radix, Bombycis corpus or Araliae Continentalis Radix for the prevention and treatment of a renal disease.

As another embodiment, this invention is to provide a health food containing the herb extracts to ensure better renal function.

This invention is described in more detail as set forth hereunder.

This invention contains extracts of one or more herb medicines selected from the group consisting of Puerariae Radix, Bombycis corpus and Araliae Continentalis Radix.

The herb extracts of this invention have demonstrated their efficacy for treatment of renal disease in animal models via measurements of blood urea nitrogen (BUN) levels, blood creatinine levels, tubular necrotic cells and degenerated glomerular cells.

BUN measures the amount of urea nitrogen, a waste product of protein metabolism, in the blood, and creatinine is a chemical waste molecule that is generated from muscle metabolism. BUN and creatinine are transported through the bloodstream to the kidneys. The kidneys filter out BUN and creatinine and dispose of them in the urine. As the kidneys become impaired, the BUN and creatinine levels in the blood will rise. Therefore, the BUN and serum creatinine have been found to be fairly reliable indicators that may evaluate the effectives of drugs in animal models with renal failure (Arch Med Res. 2004 November-December; 35(6): 484-94).

A nephron is the basic structural and functional unit of the kidney. As the number of nephrons decrease, renal function declines. As diabetic nephropathy progresses, increasing numbers of glomeruli are destroyed. The affected blood filtering function in the glomerulus may result in the glomerular degeneration. Therefore, tubular necrotic cells and degenerated glomerular cells are used as important markers of renal disease.

As a result of measuring BUN and creatinine levels in the blood, degenerated glomerular cells and tubular necrotic cells as important markers of renal disease, herb extracts of Puerariae Radix, Bombycis corpus and Araliae Continentalis Radix are more effective than Mori Cortex extract in improving renal function, although Mori Cortex has an diuretic action. When the same amount is applied, the mixed herb extract have shown better effects than a single herb extract, along with synergistic effects.

Therefore, the herb extracts of this invention can be effectively used as a pharmaceutical composition for prevention and treatment of renal disease caused by a number of different diseases, such as diabetes, hypertension, glomerulonephritis, drug toxicity (e.g., antibiotics), and urinary infection.

As another embodiment, the herb extracts of this invention are selected from herb medicines listed in the Korean Food Standard Code and can be effectively used as health foods to improve impaired renal function.

The herb extracts of this invention can be extracted from commercially available Puerariae Radix, Bombycis corpus and Araliae Continentalis Radix in such a manner that water or alcohol is added to one or more herb medicines in a weight ratio of 5 to 10 times over herbs. More than two herbs, selected from Puerariae Radix, Bombycis corpus and Araliae Continentalis Radix, are extracted, or each extract can be mixed for the herb extracts of this invention.

The herb extracts of this invention may further incorporate another herb extract for better management of impaired renal function, including Mori Cortex extract preferably. Mori Cortex extract has shown to possess a diuretic action (YAKHAK HOEJI 26(4), 197~128 (1982)), but the effectiveness of this extract for renal failure has yet to be elucidated.

The herb extracts of this invention may be prepared as soft extract under reduced pressure at 60~70° C., or as dried powder form by lyophilization or using spray drier or fluidized bed machine.

The pharmaceutical composition of this invention can have convenient routes of administration, such as oral, parenteral, dental, sublingual, nasal, rectal or subcutaneous form. The pharmaceutical composition of this invention can contain physiologically acceptable carriers to each dosage form.

For healthy people (standard body weight; 60 kg) the pharmaceutical composition of this invention may be administered at a dose of 101000 mg/day in 1-3 divided dose. The dosage and administration may vary depending on age, severity of disease and therapeutic category.

The herb extracts of this invention can be used as health food to enhance renal function. In addition to the aforementioned herb extracts, the health food of this invention may include commonly used substances in a single or mixed form in the health food sector; nutrients (vitamin, amino acid, anti-oxidant), pH modifier (citric acid, sodium citrate), sweeteners (liquid glucose, erythritol, paratinose), artificial flavors, coloring agents, expients (lactose, glucose, starch, lactulose), stabilizers, lubricants (magnesium stearate), creams (wheat germ oil, olive oil, beeswax, wax, tocopherol).

The health food of this invention may be prepared in a wide variety of oral dosage forms, such as drinks, tablets, pills, hard/soft capsules and granules, using additives acceptable in the related sector.

Advantageous Effects

This invention is to provide a pharmaceutical composition comprising herb extracts of one or more herb medicines selected from the group consisting of Puerariae Radix, Bombycis corpus or Araliae Continentalis Radix. These herb extracts can play a role to reduce the levels of BUN and blood creatinine, tubular necrotic cells and degenerated glomerular cells, thus providing a novel pharmaceutical candidate useful for prevention and treatment of renal disease as well as health food to enhance renal functions.

Thus the herb extracts of this invention can be effectively employed as pharmaceutical composition for prevention and treatment of renal disease or health food for potentiating renal functions.

BEST MODE

This invention will now be described by reference to the following examples and experimental examples which are merely illustrative and which are not to be construed as a limitation of the scope of this invention.

Example 1

Preparation of Single Extracts of Puerariae Radix, Bombycis Corpus, Araliae Continentalis Radix and Mori Cortex Puerariae Radix, Araliae Continentalis Radix, Bombycis corpus and Mori Cortex were purchased from the marketplace and assayed by the Korean Pharmacopoeia (the $8^{th}$ revised edition). Water was added to each of Puerariae Radix, Araliae Continentalis Radix, Bombycis corpus and Mori Cortex, which was found to conform to the current standards, in a weight ratio (6:1), extracted with boiling water for 2 hours and filtered to obtain the first boiling-water extract.

Water was further added to the residue in a weight ratio (6:1), extracted with boiling water for 1 hour and filtered to obtain the second boiling-water extract. A mixture of the two boiling-water extracts was lyophilized to obtain a single extract of the four herbs in powder form.

Example 2-10

Preparation of an Mixed Extract Containing the Extract of Two Herbs Selected from Puerariae Radix, Bombycis Corpus and Mori Cortex As shown in Table 1, a total of 9 powdered extracts containing two herb extracts selected from single extracts of Puerariae Radix, Bombycis corpus and Mori Cortex, so obtained in Example 1, were prepared in different weight ratios.

TABLE 1

Nine powered extracts containing two herb extracts in different weight ratios

|  | Bombycis corpus | Puerariae Radix | Mori Cortex |
|---|---|---|---|
| Example 2 | 1 | 1 | — |
| Example 3 | 3 | 1 | — |
| Example 4 | 1 | 3 | — |
| Example 5 | 1 | — | 1 |
| Example 6 | 3 | — | 1 |
| Example 7 | 1 | — | 3 |
| Example 8 | — | 1 | 1 |
| Example 9 | — | 3 | 1 |
| Example 10 | — | 1 | 3 |

Example 11

Preparation of an Mixed Extract Containing Single Extracts of Puerariae Radix, Bombycis Corpus, Araliae Continentalis Radix and Mori Cortex by a Weight Ratio (1:1:1:1)

A powdered mixed extract containing single extracts of Puerariae Radix, Bombycis corpus, Araliae Continentalis Radix and Mori Cortex, so obtained in Example 1, was prepared in a weight ratio of 1:1:1:1.

Example 12

Preparation of an Mixed Extract Containing Single Extracts of Puerariae Radix, Bombycis Corpus, Araliae Continentalis Radix and Mori Cortex by a Weight Ratio (1.1:1.9:0.9:1.3)

A powdered mixed extract containing single extracts of Puerariae Radix, Bombycis corpus, Araliae Continentalis Radix and Mori Cortex, so obtained in Example 1, was prepared in a weight ratio of 1.1:1.9:0.9:1.3, Experimental Example 1

Measurement of BUN Levels in Diabetes-Induced Animals

Because urea is cleared from the bloodstream by the kidneys, a test measuring how much urea nitrogen remains in the blood can be used as a test of renal function. Thus, the inventors measured the BUN levels in diabetes-induced animals receiving a single or mixed extract.

1. Measurement of BUN Levels in a Single Extract-Treated Groups

Single extracts prepared from Example 1 were used as test samples.

Six-week-old female SD rats were randomly allocated into six groups (five animals per group); 1) one normal group, 2) one streptozotocin-induced diabetic control group without treatment, and four streptozotocin-induced diabetic groups receiving 200 mg/kg of each test sample. Diabetes was induced in the rats by intraperitoneal administration of streptozotocin (60 mg/kg body weight). Two blood samples were collected at 3 days after the injection of streptozotocin and at 28 days after treatment with each test sample. The blood glucose level was determined using a NaF glucose vacuum tube and a blood analyzer. Measurements of the BUN level were also performed with a blood analyzer in serum. The serum analysis was performed by E-won clinical center located at Dongjak-gu, Seoul, Korea.

As shown in Table 2, the BUN levels in extract-treated rats and control were elevated, when compared to normal rats. However, significant decreases in the BUN levels were observed from animals receiving Puerariae Radix, Bombycis corpus, Araliae Continentalis Radix and Mori Cortex, compared to levels in control. In particular, more decrease in the BUN levels were observed in rats treated with Puerariae Radix, Bombycis corpus and Araliae Continentalis Radix extracts than in Mori Cortex extract.

TABLE 2

BUN levels (mg/dL, mean ± S.D.)

|  | BUN levels |
|---|---|
| Normal | 19.43 ± 0.83 |
| Control | 112.17 ± 6.88* |
| Puerariae Radix extract | 80.23 ± 6.73*,# |
| Bombycis corpus extract | 84.33 ± 16.37*,# |
| Araliae Continentalis Radix extract | 79.07 ± 5.42*,# |
| Mori Cortex extract | 84.43 ± 27.66*,# |

*$P < 0.05$ (compared to normal rats),
*$P < 0.05$ (compared to control rats)

2. Measurement of BUN Levels in Mixed Extract-Treated Groups

Mixed extracts, so prepared from Example 11, were used as test samples.

Animals were randomly divided into five groups; 1) one normal group, 2) one control group, 2) three extract-treated groups. Animals in the extract-treated groups and control group were given streptozotocin 8 days after streptozotocin. Test samples were orally given daily at three different doses of 100 mg/kg, 200 mg/kg and 300 mg/kg for 28 days from 8 days after streptozotocin dosing. Blood samples were obtained at the baseline, 5 days after streptozotocin injection and 28 days after oral administration of the test samples. Thereafter, measurements of the BUN level were performed in the same manner as did in single extracts.

As shown in Table 3, the BUN levels in normal rats remained unchanged, whereas those in the diabetes-induced control rats increased as high as 5 times. In the extract-treated rats, there were significant decreases in the BUN levels as half as those in control. The extract-treated rats at the doses of 200 mg/kg and 300 mg/kg did not show any dose-dependence and maximum therapeutic effects were determined at the dose of about 200 mg/kg.

TABLE 3

BUN levels (mg/dL, mean ± S.D.) after treatment

| Group | | Before streptozotocin injection | 5 days after streptozotocin injection | 28 days after oral administration |
|---|---|---|---|---|
| Normal | | 20.85 ± 2.34 | 21.72 ± 1.60 | 24.12 ± 2.74 |
| Control | | 19.20 ± 1.64 | 32.66 ± 8.90** | 103.08 ± 11.23* |
| Exemple 11 | 100 mg/kg | 19.00 ± 1.54 | 32.80 ± 8.02* | 57.54 ± 9.10* |
| | 200 mg/kg | 20.30 ± 1.52 | 32.00 ± 8.33* | 48.28 ± 18.27* |
| | 300 mg/kg | 19.24 ± 3.13 | 34.88 ± 7.58* | 52.94 ± 6.18* |

*$P < 0.015$,
**$P < 0.05$ (compared to normal group)

Experimental Example 2

Measurement of Tubular Necrotic Cells in Diabetes-Induced Rats

Measurements of tubular necrotic cells were performed to assess the effectiveness of herb extracts of this invention against renal disease.

1. Materials and Methods

Test samples (Examples 1, 11) were given to rats (Experimental example 1) at the dose of 200 mg/kg. The tubular necrotic cells were measured using an image analyzer.

2. Results

As shown in Table 4, the number of tubular necrotic cells in all extract-treated rats was observed lower (8 times) than that of control. Among the four single extract-treated rats, the highest inhibitory effect on the tubular necrotic cells was detected in rats treated with Puerariae Radix extract. The extract-treated rats of Bombycis corpus and Araliae Continentalis Radix showed an anti-inhibitory effect against the tubular necrosis, which was comparable to the Mori Cortex extract. Further, the inhibitory effect of the mixed extract-treated rats (Example 11) as higher (5 times) than that of other single extract-treated rats.

TABLE 4

Tubular necrotic cells (Death cells/1000 tubular cells, mean ± S.D.)

| Group | Tubular necrotic cells |
|---|---|
| Normal | 1.17 ± 0.75 |
| Control | 480.67 ± 122.38* |
| Puerariae Radix extract | 169.33 ± 39.15*,# |
| Bombycis corpus extract | 323.67 ± 57.22*,# |
| Araliae Continentalis Radix extract | 319.00 ± 73.86*,# |
| Mori Cortex extract | 320.17 ± 72.08*,# |
| Example 11 | 57.33 ± 19.94*,# |

*$P < 0.05$ (compared to normal group),
$P < 0.01$/
$P < 0.05$ (compared to control group)

Experimental Example 3

Measurement of Degenerated Glomerular Cells in Diabetes-Induced Rats

Measurements of degenerated glomerular cells were performed to assess the effectiveness of herb extracts of this invention against renal disease.

1. Materials and Methods

Using the same test samples and animals as those in Experimental example 2, the number of degenerated glomerular cells in the kidneys was calculated using an image analyzer.

2. Results

As shown in Table 5, significant increase in the number of degenerated glomerular cells was observed in streptozotocin-treated control rats, when compared to normal rats. There was significant reduction of diabetic degenerated glomerular cells in the single extract-treated rats of Puerariae Radix, Bombycis corpus, Araliae Continentalis Radix and Mori Cortex in comparison to control rats. The decreasing number of degenerated glomerular cells was markedly observed in rats treated with the extract of Puerariae Radix, Bombycis corpus and Araliae Continentalis Radix in comparison to rats treated with Mori Cortex extract. Further, rats treated with the mixed extract (Example 11) exhibited higher (about 2 times) inhibitory effect on the increase of degenerated glomerular cells than that of rats treated with other single extract.

TABLE 5

Number of degenerated glomerular cells (mean ± S.D.)

| | Number of degenerated glomerular cells |
|---|---|
| Normal | 1.83 ± 0.75 |
| Control | 79.17 ± 10.40* |
| Puerariae Radix extract | 54.50 ± 12.11*,# |
| Bombycis corpus extract | 64.33 ± 6.98*,# |
| Araliae Continentalis Radix extract | 57.00 ± 8.60*,# |
| Mori Cortex extract | 65.17 ± 8.91*,# |
| Example 11 | 35.50 ± 10.43*,# |

*$P < 0.05$ (compared to normal group),
$P < 0.01$/
$P < 0.05$ (compared to control group)

Experimental Example 4

Histopathological Test in Diabetes-Induced Rats

The degeneration and fibrosis detected in kidney can be used as the markers of renal disease (J. Pathol. 2000 March; 190(4): 484-8). Thus, histopathological test on renal tissues was performed to assess the effectiveness of herb extracts of this invention against renal disease.

1. Materials and Methods

The same test samples and animals as those in Experimental example 1 were used for this experiment.

28 days after the test samples dosing, female SD rats were fasted overnight and sacrificed by exsanguinations from vena cava. The dissected kidneys were fixed in 10% formalin and embedded in paraffin. The section were cut in 3-4 μm thicknesses and stained with hematoxylin-eosin 2. Results As nephropathy progresses due to degenerated glomerular cells and tubular necrosis, parenchymal changes associated with the fibrosis at the affected site may lead to chronic renal failure. In this context, renal fibrosis becomes an important marker for chronic renal failure.

Figure 1:
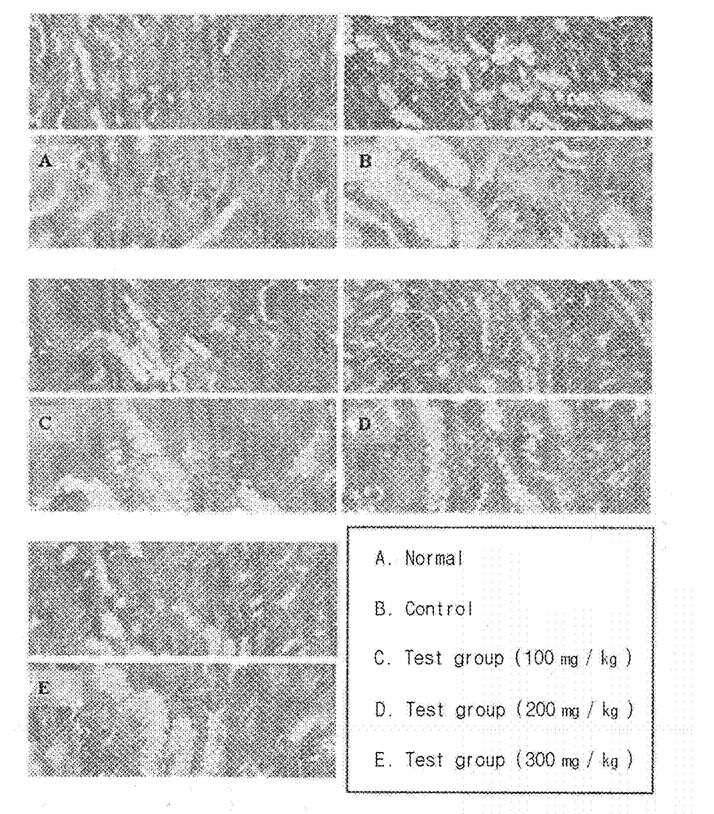
FIG. 1 is a micrograph of kidney histopathological testing.

As shown in FIG. 1 and Table 6, mild renal fibrosis occurred in all extract-treated groups by less than 40 percent in comparison all control rats. The number of degenerated cells significantly decreased in all extract-treated rats by about ⅓ to ⅕, when compared to control. Therefore, it is noted that significantly prevented elevation in the renal fibrosis and the degenerated cell was observed in the test groups, when compared to control group.

TABLE 6

Results of histopathological testing

| Category | Normal | Control | Test groups 100 mg/kg | 200 mg/kg | 300 mg/kg |
|---|---|---|---|---|---|
| Renal Fibrosis | 0/5 (0%) | 5/5 (100%) | 2/5 (40%) | 1/4 (25%) | 1/5 (20%) |
| 1+ | 0/5 (0%) | 3/5 (60%) | 2/5 (40%) | 1/4 (25%) | 1/5 (20%) |
| 2+ | 0/5 (0%) | 2/5 (40%) | 0/5 (0%) | 0/4 (0%) | 0/5 (0%) |
| Change of number of degenerated cells | 1.40 ± 1.14 | 346.60 ± 68.23* | 123.00 ± 21.21* | 87.40 ± 30.05*,# | 66.80 ± 30.13*,# |

Degrees of gross finding, 1+: Slight appearance; +2: Moderate appearance.

Experimental Example 5

Measurement of BUN Levels in Rats with Subacute Renal Failure

The mixed extracts, so prepared in Example 12, were used as test samples.

Six-week-old female SD rats were randomly allocated into seven groups (eight animals per group); 1) one normal group, 2) one control group showing subacute renal failure induced by carbon tetrachloride ($CCl_4$), 3) captopril (CAPT) 100 mg/kg group as positive control, 4) silymarin (SILY) 25 mg/kg group as positive control, and 5) three extract-treated groups at the doses of 50 mg/kg, 100 mg/kg, and 200 mg/kg.

After $CCl_4$ was administered to rats, test samples were daily given simultaneously at the doses of 50 mg/kg, 100 mg/kg, and 200 mg/kg for 42 days. CAPT 100 mg/kg and SILY 25 mg/kg were orally administered to animals in the same manner as above.

The blood glucose level was determined using a NaF glucose vacuum tube. Measurements of the BUN level were also performed with a blood analyzer in serum. The serum analysis was performed by E-won clinical center located at Dongjak-gu, Seoul, Korea.

As shown in Table 7, the BUN levels in vehicle-treated control rats were significantly higher (p<0.01) than those of normal rats, and after $CCl_4$ administration were significantly raised (p<0.01) than those of normal rats. The BUN levels in the treatments rats were significantly lower (p<0.01 or p<0.05) than those of vehicle-treated control rats. Except for SILY-treated rats, the BUN levels in all extract-treated rats were significantly lowered (p<0.01 or p<0.05) after $CCl_4$ administration.

The BUN levels in SILY-treated rats were markedly reduced in a dose-dependant pattern in comparison to vehicle-treated control rats, although there was no significance in changes of the BUN levels. Therefore, it is noted that herb extracts of this invention prevented the elevation of BUN levels.

TABLE 7

Measurements of BUN levels

| Group | Before $CCl_4$ administration | 42 days after administration of $CCl_4$ and test samples |
|---|---|---|
| Normal | 18.39 ± 2.76 | 20.43 ± 2.22 |
| Control | 17.96 ± 2.64 | 31.38 ± 4.07* |
| Positive control (captopril) | 18.28 ± 1.13 | 23.88 ± 2.38**,# |
| Positive control (silymarin) | 17.95 ± 1.97 | 26.68 ± 2.35*,## |
| Test groups 50 mg/kg | 18.58 ± 2.47 | 26.15 ± 2.55*,## |
| Test groups 100 mg/kg | 17.43 ± 2.44 | 24.60 ± 1.69*,# |
| Test groups 200 mg/kg | 17.84 ± 1.99 | 24.06 ± 3.11# |

*P < 0.01,
**P < 0.05 (compared to normal group);
P < 0.01,
P < 0.05 (compared to control group)

Experimental Example 6

Measurement of Blood Creatinine Levels in Rats with Subacute Renal Failure

Measurements of blood creatinine levels were performed to assess the effectiveness of herb extracts of this invention against renal disease.

1. Materials and Methods

The same test samples and animals as those in Experimental example 5 were used for this experiment. At sacrifice, the blood creatinine levels were measured using collected blood samples.

2. Results

As shown in Table 8, the blood creatinine levels in vehicle-treated control rats were significantly higher (p<0.01) than those of normal rats and were significantly raised (p<0.01) than those of normal rats after $CCl_4$ was given.

The creatinine levels in the extract-treated rats were significantly lower (p<0.01) than those of vehicle-treated control. The blood creatinine levels in all extract-treated groups were significantly lowered (p<0.01) than those of control after $CCl_4$ administration.

The blood creatinine levels in the extract-treated rats were reduced in a dose-dependant pattern in comparison to those of vehicle-treated control rats. Therefore, it is noted that herb extracts of this invention prevented significant elevation of the blood creatinine levels.

TABLE 8

Blood creatinine levels

| Group | Before $CCl_4$ administration | 42 days after administration of $CCl_4$ and test samples |
|---|---|---|
| Normal | 0.58 ± 0.04 | 0.63 ± 0.06 |
| control | 0.58 ± 0.03 | 0.81 ± 0.12* |
| Positive control (captopril) | 0.58 ± 0.03 | 0.63 ± 0.04# |
| Positive control (silymarin) | 0.57 ± 0.03 | 0.62 ± 0.05# |

TABLE 8-continued

Blood creatinine levels

| Group | | Before $CCl_4$ administration | 42 days after administration of $CCl_4$ and test samples |
|---|---|---|---|
| Test groups | 50 mg/kg | 0.59 ± 0.04 | 0.66 ± 0.04# |
| | 100 mg/kg | 0.57 ± 0.03 | 0.62 ± 0.05# |
| | 200 mg/kg | 0.58 ± 0.04 | 0.61 ± 0.04# |

*P < 0.01 (compared to normal group);
P < 0.01 (compared to control group)

Experimental Example 7

Measurement of Degenerated Glomerular Cells in Rats with Subacute Renal Failure

The same samples and animals as those in Experimental example 5 were used. The number of degenerated glomerular cells was measured in the manner as Experimental example 3 to assess the effectiveness of herb extracts of this invention against renal disease.

There was no abnormal finding in the tubule, but the renal failure featuring increased glomerular cells and vasodilated atrophic glomerulus cells was observed in all of $CCl_4$-treated rats was observed. The histopathological neuropathy was significantly reduced in all treatment groups.

As shown in Table 9, the number of degenerated glomerular in vehicle-treated control rats was significantly higher (p<0.01) than that in normal rats. The number of degenerated glomerular cells in the extract-treated rats was significantly lower (p<0.01) histomorphometrically in a dose-dependent pattern than that in vehicle-treated control rats.

As such, the herb extracts of this invention is thought to be effective for the treatment of neuropathy including $CCl_4$-induced subacute renal failure, while showing the protective effect of kidneys similar to an equivalent amount of CAPT.

The herb extract group at 50 mg/kg showed a protective effect of kidneys similar to SILY 25 mg/kg group. The effective dose of the herb extract group for $CCl_4$-induced subacute renal failure was in the range of 50 mg/kg or less.

TABLE 9

Measurements of degenerated glomerular cells

| | | Number of degenerated glomerular cells |
|---|---|---|
| Normal | | 2.00 ± 1.31 |
| Control | | 77.38 ± 10.61* |
| Positive control (captopril) | | 45.75 ± 12.54*,# |
| Positive control (silymarin) | | 47.13 ± 12.32*,# |
| Test groups | 50 mg/kg | 55.13 ± 11.33*,# |
| | 100 mg/kg | 35.75 ± 7.69*,# |
| | 200 mg/kg | 24.13 ± 16.92*,# |

*P < 0.01 (compared to normal group);
P < 0.01 (compared to control group)

Experimental Example 8

Measurement of BUN Levels in Rats with Acute Renal Failure

The mixed extracts, so prepared in Example 12, were used as test samples. Six-week-old female SD rats were randomly allocated into seven groups (eight animals per group); 1) one normal group, 2) one control group showing acute renal failure induced by cisplatin (CCDP), 3) captopril (CAPT) 100 mg/kg group as positive control, 4) losartan (LOSA) 20 mg/kg group as positive control, and 5) three extract-treated groups at the doses of 50 mg/kg, 100 mg/kg, and 200 mg/kg. Test samples at the doses of were orally administered to animals at the doses of 50 mg/kg, 100 mg/kg, and 200 mg/kg in a period ranging from 28 days before CCDP administration to 4 days after CCDP administration. Five days after CCDP administration, all animals were sacrificed to assess the BUN levels.

The test results between rats receiving both CAPT 100 mg/kg and LOSA 20 mg/kg were compared. For a period that test samples were administered to animals (28 days before CCDP administration), similar changes in the BUN levels were observed in both normal and control rats. During that period careful observation was made to rats receiving 200 mg/kg of the test sample and LOSA-treated rats to assess their significance (p<0.05) over control.

As shown in Table 10, the BUN levels in all extract-treated rats were significantly reduced. Following CCDP administration, the BUN levels in vehicle-treated control rats was significantly higher (p<0.01) than those of normal rats. However, the BUN levels in all of drug-treated rats were significantly lower (p<0.01 or p<0.05) than those of vehicle-treated control rats.

TABLE 10

Measurements of BUN levels

| Group | | Before cisplatin administration | 5 days after cisplatin administration | 28 days after administration of test samples |
|---|---|---|---|---|
| Normal | | 16.91 ± 1.99 | 19.93 ± 1.87 | 20.24 ± 1.81 |
| Control | | 16.89 ± 1.53 | 205.98 ± 98.27* | 20.10 ± 1.53 |
| Positive control(captopril) | | 17.05 ± 2.72 | 94.53 ± 59.63*,# | 18.24 ± 1.18**,## |
| Positive control(losartan) | | 16.88 ± 2.16 | 77.34 ± 48.68*,# | 17.25 ± 1.45*,# |
| Extract-treated groups | 50 mg/kg | 17.21 ± 2.57 | 85.66 ± 32.23*,# | 18.43 ± 2.95 |
| | 100 mg/kg | 16.83 ± 1.92 | 75.88 ± 53.90**,# | 18.35 ± 1.84## |
| | 200 mg/kg | 16.73 ± 2.18 | 72.64 ± 53.66*,# | 16.75 ± 2.75**,## |

*P < 0.01,
**P < 0.05 (compared to normal group);
P < 0.01,
P < 0.05 (compared to control group)

Experimental Example 9

Measurement of Blood Creatinine Levels in Rats with Acute Renal Failure

Measurements of blood creatinine levels were performed to assess the effectiveness of herb extracts of this invention against renal disease.

1. Materials and Methods

The same samples and animals as those in Experimental example 8 were used. Animals were sacrificed, and the blood creatinine levels were measured using collected blood samples.

2. Results

For a period that test samples were administered to animals (28 days before CCDP administration), similar changes in the blood creatinine levels were observed in both normal and control rats. During that period careful observation was made to rats receiving 200 mg/kg of the test sample and LOSA-treated rats to assess their significance ($p<0.05$) over control.

As shown in Table 11, the blood creatinine levels in all extract-treated rats were significantly reduced except for rats treated with 100 mg/kg of the extract. Following CCDP administration, the blood creatinine levels in vehicle-treated control rats ware significantly higher ($p<0.01$) than normal rats. However, the blood creatinine levels in all of drug-treated rats were significantly lower ($p<0.01$ or $p<0.05$) than vehicle-treated control rats.

TABLE 11

Measurement of blood creatinine levels

|  |  | Before cisplatin administration | 5 days after cisplatin administration | 28 days after administration of test samples |
|---|---|---|---|---|
| Normal |  | 0.55 ± 0.05 | 0.66 ± 0.06 | 0.63 ± 0.05 |
| Control |  | 0.57 ± 0.03 | 3.76 ± 2.41* | 0.65 ± 0.05 |
| captopril |  | 0.58 ± 0.04 | 1.65 ± 0.83*,# | 0.62 ± 0.02 |
| Losartan |  | 0.57 ± 0.03 | 1.60 ± 0.98*,# | 0.60 ± 0.03## |
| Extract- | 50 mg/kg | 0.57 ± 0.03 | 1.56 ± 0.66*,# | 0.64 ± 0.03 |
| treated | 100 mg/kg | 0.56 ± 0.02 | 1.52 ± 0.95*,# | 0.64 ± 0.03 |
| groups | 200 mg/kg | 0.57 ± 0.02 | 1.46 ± 0.81*,# | 0.59 ± 0.03## |

*$P < 0.01$,
**$P < 0.05$ (compared to normal group);
$P < 0.01$,
$P < 0.05$ (compared to control group)

Experimental Example 10

Measurement of Degenerated Renal Areas in Rats with Acute Renal Failure

The number of degenerated renal areas was measured to assess the effectiveness of herb extracts of this invention against renal disease.

The same samples and animals as those in Experimental example 8 were used.

The renal failure featuring a focal degeneration, such as epithelial necrosis and degenerative changes in the tubule was observed in all of CCDP-treated rats. As shown in Table 12, the histopathological neuropathy was significantly reduced in all treatment groups. The ratio of degenerative parenchymal tissue in the kidneys observed in vehicle-treated control rats was significantly higher ($p<0.01$) than those of normal rats, whereas the number of degenerated renal cells in the extract-treated rats was significantly lower ($p<0.01$) histomorphometrically in a dose-dependent pattern than those of vehicle-treated control rats. The herb extract group at 50 mg/kg showed comparable or better protective effect of kidneys than CAPT 100 mg/kg and LOSA 20 mg/kg groups.

As such, the herb extracts of this invention is thought to be effective for the treatment of neuropathy including CCDP-induced acute renal failure,

TABLE 12

Measurements of degenerated renal area

|  |  | Number of degenerated renal areas |
|---|---|---|
| Normal |  | 1.73 ± 1.60 |
| Control |  | 78.92 ± 8.56* |
| Positive control(captopril) |  | 56.76 ± 10.36*,# |
| Positive control(losartan) |  | 63.80 ± 10.24*,## |
| Test | 50 mg/kg | 50.39 ± 7.47*,# |
| groups | 100 mg/kg | 36.29 ± 7.38*,# |
|  | 200 mg/kg | 30.40 ± 7.07*,# |

*$P < 0.01$ (compared to normal group);
$P < 0.01$,
$P < 0.05$ (compared to control group)

Experimental Example 11

Measurement of BUN Levels in Rats with Acute Renal Failure

The mixed extracts, so prepared in Examples 2-10, were used as test samples.

Six-week-old female SD rats were randomly allocated into 13 groups (five animals per group); 1) one normal group, 2) one control group showing acute renal failure induced by cisplatin (CCDP), 3) captopril (CAPT) 100 mg/kg group as positive control, 4) one positive group treated with 200 mg/kg of the extract (Example 12), and 5) nine groups showing acute renal failure induced by CCDP and treated with 200 mg/kg of the extracts (Examples 2-10).

Test samples were orally administered to animals at the dose of 200 mg/kg in a period ranging from 23 days before CCDP administration to 4 days after CCDP administration. Five days after CCDP administration, all animals were sacrificed to assess the BUN levels.

The test results compared with two positive control groups. As shown in Table 13, the BUN levels in vehicle-treated control rats were significant higher ($p<0.01$) than those of normal rats. However, the BUN levels in all of drug-treated rats were significantly lower ($p<0.01$ or $p<0.05$) than those of vehicle-treated control rats, except for Examples 5-7 (Bombycis corpus:Mori Cortex=1:1, 3:1, 1:3).

The BUN levels in rats treated with the extracts of Example 6-7 (Bombycis corpus:Mori Cortex=3:1, 1:3) were non-significantly but showed a slight reduction compared with vehicle-treated control rats. The treatment group of Example 5 (Bombycis corpus:Mori Cortex=1:1) showed extremely similar BUN levels to vehicle-treated control. It was noted that the elevation of the BUN levels in rats with CCDP-induced acute renal failure was markedly prevented by the extract of Example 8 (Puerariae Radix:Mori Cortex=1:1). In particular, the extract of Example 8 (Puerariae Radix:Mori Cortex=1:1) was superior to that of Example 12 in inhibiting the BUN levels.

TABLE 13

Measurements of BUN levels treated with test samples

| Category | BUN levels (mg/dL) |
|---|---|
| Normal | 19.64 ± 2.41 |
| Control | 163.04 ± 28.67* |
| Positive control (captopril) | 96.82 ± 35.08*,## |
| Positive control (Test sample from Example 12) | 63.38 ± 15.11*,# |
| Example 2 (Bombycis corpus:Puerariae Radix = 1:1) | 81.84 ± 35.82*,## |
| Example 3 (Bombycis corpus:Puerariae Radix = 3:1) | 95.62 ± 38.88*,## |
| Example 4 (Bombycis corpus:Puerariae Radix = 1:3) | 82.18 ± 36.09*,## |
| Example 5 (Bombycis corpus:Mori Cortex = 1:1) | 162.88 ± 31.57* |
| Example 6 (Bombycis corpus:Mori Cortex = 3:1) | 146.36 ± 45.62* |
| Example 7 (Bombycis corpus:Mori Cortex = 1:3) | 145.74 ± 22.19* |
| Example 8 (Puerariae Radix:Mori Cortex = 1:1) | 51.18 ± 17.98*,# |
| Example 9 (Puerariae Radix:Mori Cortex = 3:1) | 86.86 ± 60.37*,## |
| Example 10 (Puerariae Radix:Mori Cortex = 1:3) | 85.04 ± 39.81*,## |

*$P < 0.01$,
**$P < 0.05$ (compared to normal group);
$P < 0.01$,
$P < 0.05$ (compared to control group)

Experimental Example 12

Measurement of Blood Creatinine Levels in Rats with Acute Renal Failure

Measurements of blood creatinine levels were performed to assess the effectiveness of the two mixed extracts of this invention against renal disease.

1. Materials and Methods

The same test samples and animals as those in Experimental example 11 were used for this experiment. At sacrifice, the blood creatinine levels were measured using collected blood samples.

2. Results

As shown in Table 14, the blood creatinine levels in vehicle-treated control rats were significant higher (p<0.01) than those of normal rats. However, the blood creatinine levels in all of drug-treated rats were significantly lower (p<0.01 or p<0.05) than those of vehicle-treated control rats, except for Examples 5-7 (Bombycis corpus:Mori Cortex=1:1, 3:1, 1:3).

The creatinine levels in rats treated with the extracts of Example 6-7 (Bombycis corpus:Mori Cortex=3:1, 1:3) were insignificant but showed a slight reduction compared with vehicle-treated control rats. The treatment group of Example 5 (Bombycis corpus:Mori Cortex=1:1) showed extremely similar creatinine levels to vehicle-treated control.

It was noted that the elevation of the creatinine levels in rats with CCDP-induced acute renal failure was markedly prevented by the extract of Example 8 (Puerariae Radix:Mori Cortex=1:1), especially when compared to the extract of Example 12 in inhibiting the blood creatinine levels.

TABLE 14

Measurements of blood creatinine levels

| Category | Blood creatinine levels (mg/dL) |
|---|---|
| Normal | 0.57 ± 0.05 |
| Control | 2.34 ± 0.69* |
| Positive control (captopril) | 1.36 ± 0.27*,## |
| Positive control (Test sample from Example 12) | 1.04 ± 0.31**,# |
| Example 2 (Bombycis corpus:Puerariae Radix = 1:1) | 1.01 ± 0.26**,# |
| Example 3 (Bombycis corpus:Puerariae Radix = 3:1) | 1.22 ± 0.58*,## |
| Example 4 (Bombycis corpus:Puerariae Radix = 1:3) | 1.30 ± 0.35*,## |
| Example 5 (Bombycis corpus:Mori Cortex = 1:1) | 2.81 ± 1.49* |
| Example 6 (Bombycis corpus:Mori Cortex = 3:1) | 2.20 ± 0.47* |
| Example 7 (Bombycis corpus:Mori Cortex = 1:3) | 2.25 ± 0.62* |
| Example 8 (Puerariae Radix:Mori Cortex = 1:1) | 0.57 ± 0.13# |
| Example 9 (Puerariae Radix:Mori Cortex = 3:1) | 1.11 ± 0.33*,## |
| Example 10 (Puerariae Radix:Mori Cortex = 1:3) | 1.11 ± 0.64## |

*$P < 0.01$,
**$P < 0.05$ (compared to normal group);
$P < 0.01$,
$P < 0.05$ (compared to control group)

Experimental Example 13

Measurement of Degenerated Renal Areas in Rats with Acute Renal Failure

The same samples and animals as those in Experimental example 11 were used. The number of degenerated renal areas was histopathologically measured to assess the effectiveness of herb extracts of this invention against renal disease.

The renal failure featuring a focal degeneration, such as epithelial necrosis and degeneration in the tubule was observed in all of CCDP-treated rats. As shown in Table 15, the histopathological neuropathy was significantly reduced in all treatment groups.

The ratio of degenerative parenchymal tissue in the kidneys observed in vehicle-treated control rats was significantly higher (p<0.01) than that in normal rats, whereas the number of degenerated regions in the extract-treated rats was significantly lower (p<0.01 or p<0.05) histomorphometrically than that in vehicle-treated control rats, except for Examples 5-7 (Bombycis corpus:Mori Cortex=1:1, 3:1, 1:3).

It was noted that focal degeneration in rats with acute renal failure induced by CCDP was markedly prevented by the extract of Example 8 (Puerariae Radix:Mori Cortex=1:1), especially when compared to the extract of Example 12 in inhibiting the focal degeneration.

TABLE 15

Measurements of degenerated renal area

| Category | Number of degenerated renal areas (mg/dL) |
|---|---|
| Normal | 4.52 ± 3.44 |
| Control | 79.44 ± 6.51* |
| Positive control (captopril) | 58.40 ± 8.85*,# |
| Positive control (Test sample from Example 12) | 37.90 ± 9.27*,# |
| Example 2 (Bombycis corpus:Puerariae Radix = 1:1) | 54.75 ± 4.72*,## |
| Example 3 (Bombycis corpus:Puerariae Radix = 3:1) | 64.46 ± 9.70*,## |
| Example 4 (Bombycis corpus:Puerariae Radix = 1:3) | 68.72 ± 11.20* |
| Example 5 (Bombycis corpus:Mori Cortex = 1:1) | 77.24 ± 6.28* |
| Example 6 (Bombycis corpus:Mori Cortex = 3:1) | 73.68 ± 13.10* |

TABLE 15-continued

Measurements of degenerated renal area

| Category | Number of degenerated renal areas (mg/dL) |
|---|---|
| Example 7 (Bombycis corpus:Mori Cortex = 1:3) | 68.52 ± 8.08*,## |
| Example 8 (Puerariae Radix:Mori Cortex = 1:1) | 36.33 ± 5.85*,# |
| Example 9 (Puerariae Radix:Mori Cortex = 3:1) | 53.34 ± 7.41*,# |
| Example 10 (Puerariae Radix:Mori Cortex = 1:3) | 51.44 ± 10.11*,# |

*P < 0.01 (compared to normal group);
P < 0.01,
P < 0.05 (compared to control group)

Experimental Example 14

Acute Toxicity Test

1. Materials and Methods

Six-week-old male and female SPF (specific pathogen-free) ICR mice were randomly allocated (five animals per group). Single extracts of Puerariae Radix, Araliae Continentalis Radix and Bombycis corpus (Example 1) and mixed extracts of these herbs (Example 12) suspended before administration in 0.5% methylcellulose solution was orally given to mice at single doses of 2000 mg/kg, 1000 mg/kg, 500 mg/kg, 250 mg/kg and 125 mg/kg, respectively. For all animals treated with the test samples, general signs, body weight and dead animals were observed. After all survivors were necropsied, organs and tissues, such as abdominal cavity and thoracic cavity, were grossly examined. In addition, 12 specific organs were microscopically observed.

2. Results

No clinical signs or symptoms, or dead animals were observed in animals treated with the test samples. There was no toxicity sign symptom in terms of body weight or autopsy findings. The oral $LD_{50}$ of the herb extract of this invention was more than 2000 mg/kg in mice.

Experimental Example 15

Toxicity Test for Repeated Two-Week Dosing

1. Materials and Methods

Six-week-old male and female SPF (specific pathogen-free) ICR mice were randomly allocated into 12 groups (five animals per group). Single extracts of Puerariae Radix, Araliae Continentalis Radix and Bombycis corpus (Example 1) and mixed extracts of these herbs (Example 12) suspended before administration in sterile distilled water was orally given to mice at single doses of 2000 mg/kg, 1000 mg/kg, 500 mg/kg, 250 mg/kg and 125 mg/kg, respectively for the duration of two weeks. For all animals treated with the test samples, general signs, body weight and dead animals were observed. After all survivors were necropsied, organs and tissues, such as abdominal cavity and thoracic cavity, were macroscopically examined.

2. Results

Loss of body weigh and food intake in mice receiving the dose of 2000 mg/kg was observed. As abnormal findings were not reported until the maximum dose of 2000 mg/kg, the maximum tolerance dose for repeated two-week dosing was more than 2000 mg/kg in both sexes.

Therefore, it was suggested that the maximum dose for a 4-week repeated administration was 2000 mg/kg/10 ml/day in both sexes. The medium and low regimens are preferably 1000 mg/kg/10 ml/day and 500 mg/kg/10 ml/day, respectively.

This invention will now be described by reference to the following manufacturing examples, which are merely illustrative and which are not to be construed as a limitation of the scope of this invention.

Manufacturing Example 1

Tablet Form

1. Tablet Form Containing Puerariae Radix Extract

Using a common manufacturing process, a tablet form containing Puerariae Radix extract was prepared in weight ratios of a single Puerariae Radix extract (Example 1; 70.0 wt. %), lactose (17.5 wt. %), magnesium stearate (5.0 wt. %), vitamin C (2.5 wt. %), and mannitol (5.0 wt. %).

2. Table Form Containing Bombycis Corpus Extract

A tablet form containing Bombycis corpus extract (single Bombycis corpus extract of Example 1; 70.0 wt. %) was prepared in the same procedure as did in the tablet form containing Puerariae Radix extract.

3. Table Form Containing Araliae Continentalis Radix Extract

A tablet form containing Araliae Continentalis Radix extract (single Araliae Continentalis Radix extract of Example 1; 70.0 wt. %) was prepared in the same procedure as did in the tablet form containing Puerariae Radix extract.

4. Table Form Containing Mixed Extract

A tablet form containing mixed extracts of Puerariae Radix, Bombycis corpus, Araliae Continentalis Radix and Mori Cortex (mixed herb extract of Example 12; 70.0 wt. %) was prepared in the same procedure as did in the tablet form containing Puerariae Radix extract.

Manufacturing Example 2

Capsule Form

1. Capsule Form Containing Puerariae Radix Extract

Using a common manufacturing process, a capsule form containing Puerariae Radix extract was prepared in weight ratios of a single Puerariae Radix extract (Example 1; 85.0 wt. %), carboxymethyl cellulose (10.0 wt. %), and magnesium stearate (5.0 wt. %).

2. Capsule Form Containing Bombycis Corpus Extract

A capsule form containing Bombycis corpus extract (single Bombycis corpus extract of Example 1; 85.0 wt. %) was prepared in the same procedure did in the capsule form containing Puerariae Radix extract.

3. Capsule Form Containing Araliae Continentalis Radix Extract

A capsule form containing Araliae Continentalis Radix extract (single Araliae Continentalis Radix extract of Example 1; 85.0 wt. %) was prepared in the same procedure did in the capsule form containing Puerariae Radix extract.

4. Table Form Containing Mixed Extract

A capsule form containing mixed extracts of Puerariae Radix, Bombycis corpus, Araliae Continentalis Radix and Mori Cortex (mixed herb extract of Example 12; 85.0 wt. %) was prepared in the same procedure as did in the capsule form containing Puerariae Radix extract.

Manufacturing Example 3

Preparation of Herb Drinks

1. Herb Drink Containing a Single Puerariae Radix Extract

Using a common method, a single herb drink containing Puerariae Radix extract (prepared from Example 1) was prepared in a manner that Puerariae Radix extract (5 wt. %) was blended with a mixture consisting of sugar (7.78 wt. %), citric acid (0.11 wt. %), flavor (0.1 wt. %) and purified water (87.01 wt. %).

2. Herb Drink Containing Bombycis Corpus Extract

A herb drink containing Bombycis corpus extract (prepared from Example 1; 5.0 wt. %) and other materials was prepared in the same manner as did in the herb drink containing the Puerariae Radix extract.

3. Herb Drink Containing Araliae Continentalis Radix Extract

A herb drink containing Araliae Continentalis Radix extract (prepared from Example 1; 5.0 wt. %) and other materials was prepared in the same manner as did in the herb drink containing the Puerariae Radix extract.

4. Herb Drink Containing Mixed Extract

A herb drink containing mixed extracts of Puerariae Radix, Bombycis corpus, Araliae Continentalis Radix, and Mori Cortex (prepared from Example 12; 5.0 wt. %) and other materials was prepared in the same manner as did in the herb drink containing the Puerariae Radix extract.

What is claimed is:

1. A method for treating nephropathy comprising administering to a subject in need thereof an effective amount of a composition consisting essentially of a water or alcohol extract of Puerariae Radix and a water or alcohol extract of Mori Cortex as active ingredients at a dry weight ratio of 1:3 to 3:1.

2. The method according to claim 1, wherein the dry weight ratio of the water or alcohol extract of Puerariae Radix and the water or alcohol extract of Mori Cortex is about 1:1.

3. The method according to claim 1, wherein the nephropathy is a renal disease induced by diabetic complications.

4. The method according to claim 1, wherein the nephropathy is a renal disease induced by nephrotoxicity.

5. The method according to claim 1, wherein the extract of Puerariae Radix and the extract of Mori Cortex are in a form of a liquid, a soft extract or a dried powder obtained by lyophilization, or spray drying, or drying using a fluidized bed machine.

* * * * *